United States Patent
Johnson et al.

(10) Patent No.: US 9,748,609 B2
(45) Date of Patent: Aug. 29, 2017

(54) DETECTION OF DEFECTS IN SOLID-POLYMER COATINGS USING REDUCTION-OXIDATION PROBES

(71) Applicant: PRIETO BATTERY, INC., Fort Collins, CO (US)

(72) Inventors: Derek C. Johnson, Johnstown, CO (US); Amy L. Prieto, Fort Collins, CO (US); Matthew Rawls, Aurora, CO (US); Wesley A. Hoffert, Fort Collins, CO (US)

(73) Assignee: Prieto Battery, Inc., Fort Collins, CO (US)

( * ) Notice: Subject to any disclaimer, the term of this patent is extended or adjusted under 35 U.S.C. 154(b) by 568 days.

(21) Appl. No.: 14/058,512

(22) Filed: Oct. 21, 2013

(65) Prior Publication Data

US 2014/0174954 A1    Jun. 26, 2014

Related U.S. Application Data

(60) Provisional application No. 61/715,943, filed on Oct. 19, 2012.

(51) Int. Cl.
*G01N 27/48* (2006.01)
*H01M 10/0585* (2010.01)
(Continued)

(52) U.S. Cl.
CPC .......... *H01M 10/0585* (2013.01); *C09D 5/24* (2013.01); *C09D 5/4407* (2013.01); *G01N 17/02* (2013.01);
(Continued)

(58) Field of Classification Search
CPC ............................... G01N 17/02; G01N 27/48
See application file for complete search history.

(56) References Cited

U.S. PATENT DOCUMENTS

| | | | |
|---|---|---|---|
| 4,685,415 | A | 8/1987 | Wegner |
| 8,142,632 | B2 | 3/2012 | Watanabe et al. |
| 2009/0226773 | A1 | 9/2009 | Takekawa |

FOREIGN PATENT DOCUMENTS

| | | |
|---|---|---|
| WO | 02095810 | 11/2002 |
| WO | 2007104058 A2 | 9/2007 |
| WO | 2013019983 | 2/2013 |

OTHER PUBLICATIONS

Che et al., "Voltammetry of the defect sites at a self-assembled monolayer on a gold surface," Journal of Electroanalytical Chemistry 453 (1998) 9-17.*

(Continued)

*Primary Examiner* — Alexander Noguerola
(74) *Attorney, Agent, or Firm* — Cochran Freund & Young LLC; Samuel M. Freund

(57) ABSTRACT

Electrochemical methods for probing solid polymer electrolyte surface coatings on electrically conducting, active, three-dimensional electrode materials for use in lithium-ion batteries, to quantitatively determine the conformity, uniformity, and the presence of pinholes, and/or other defects in coatings, without requiring the detachment of the coating from the electrode or otherwise inducing damage to the coating, are described. Coated electrodes are submersed in an electrolyte solution containing a redox-active probe species which does not induce electrochemical damage to either the working electrode or the solid polymer electrolyte surface coating. For coated $Cu_2Sb$ working electrodes, molecules including a water-soluble redox active viologen moiety have been found to be effective. The current as a function of the applied potential for an uncoated working electrode is used as a baseline for testing solid polymer surface coatings on working electrodes, and the difference in the observed current between the electrodes for a given potential is a quantitative indicator of the ability of the probe species to (Continued)

access the surface of the working electrode through the solid polymer electrolyte coating.

24 Claims, 11 Drawing Sheets

(51) Int. Cl.
| | | |
|---|---|---|
| *G01N 17/02* | (2006.01) | |
| *H01M 2/14* | (2006.01) | |
| *H01M 2/16* | (2006.01) | |
| *G01N 27/26* | (2006.01) | |
| *C09D 5/24* | (2006.01) | |
| *C09D 5/44* | (2006.01) | |
| *H01M 10/0525* | (2010.01) | |

(52) U.S. Cl.
CPC ............. *G01N 27/26* (2013.01); *G01N 27/48* (2013.01); *H01M 2/145* (2013.01); *H01M 2/1653* (2013.01); *H01M 10/0525* (2013.01); *Y10T 29/49115* (2015.01)

(56) References Cited

OTHER PUBLICATIONS

Electrochemical Series Table 1 in the CRC Handbook of Chemistry and Physics, 96th ed., 2015, pp. 5-80 to 5-84.*
International Search Report, International Searching Authority, dated Feb. 24, 2014, pp. 1-24.

* cited by examiner

DETECTION OF DEFECTS IN SOLID-POLYMER COATINGS USING REDUCTION-OXIDATION PROBES

CROSS-REFERENCE TO RELATED APPLICATIONS

The present application claims the benefit of U.S. Provisional Patent Application No. 61/715,943 for "Methods For Electropolymerizing A Solid Polymer Electrolyte And Use Within Lithium-Ion Batteries," by Daniel J. Bates et al., which was filed on Oct. 19, 2012, the contents of which application is hereby specifically incorporated by reference herein for all that it discloses and teaches.

FIELD OF THE INVENTION

The present invention relates generally to electrochemical energy storage devices and, more particularly, to an in-situ, nondestructive method for determining whether a solid polymer coating for controlling the transport of species to the surface of a coated electrode in an energy storage device is free of defects and pinholes.

BACKGROUND OF THE INVENTION

For lithium-ion batteries, the power density is inversely proportional to the lithium-ion transport length. Three-dimensional interpenetrating electrodes have been proposed in which the negative and positive electrode is separated by a thin, conformal electrode coating having submicron and nanoscale dimensions, which controls the transport of charged species such as lithium cations and electrons. In addition to a thin coating separating the electrodes, the negative and positive electrodes are interpenetrating. By directly coating one of the three-dimensional electrodes with the thin coating, however, the two-dimensional planar porous membrane sheets may be replaced. To complete the cell, the second electrode is subsequently applied to the surface of the thin coating.

Quantifying the presence, or absence, of defects or pinholes for such three-dimensional architectures is problematic since the coatings are formed during the fabrication of the energy storage device, unlike for traditional membrane separators that are first manufactured and tested before being incorporated into the electrochemical energy storage device. Such imperfections could result in the unregulated transport of reactive and or charged species through the coating, thereby resulting in unsatisfactory device performance. Further, physical removal of the coating from the electrode surface for subsequent testing would result in irreparable damage to both the coating and the energy storage device.

SUMMARY OF THE INVENTION

Embodiments of the present invention overcome the disadvantages and limitations of prior art by providing a method for probing electrode surface coatings for defects and pinholes.

Another object of embodiments of the present invention is to provide a method for probing electrode surface coatings for defects and pinholes without inducing damage to the coating.

Another object of embodiments of the present invention is to provide a method for probing electrode surface coatings for defects and pinholes without inducing damaging oxidation or reduction reactions (corrosion) within the electrode itself.

Still another object of embodiments of the present invention is to provide a method for probing electrode surface coatings having high surface areas for defects and pinholes without inducing damage to the coating.

Yet another object of embodiments of the present invention is to provide a method for probing electrode surface coatings having high surface areas irregular surfaces for defects and pinholes without inducing damage to the coating.

Another object of embodiments of the present invention is to provide a method for probing electrode surface coatings without having to physically remove the coating from the electrode surface.

Additional objects, advantages and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the method for quantitatively determining the presence of pinholes in a coating on the surface of a conductive electrode material, hereof includes: submersing the coated electrode material in a solution comprising a probe species dissolved in a solvent, wherein the reduction potential of the electrode material falls outside of the electrochemical window of the solvent, while the oxidation potential thereof falls within the window, and wherein the probe species has an electrochemical reduction potential more positive than the electrochemical reduction potential of the solvent and an electrochemical oxidation potential more negative than the electrochemical oxidation potential of the electrode; applying a potential to the coated electrode material relative to a second electrode submersed in the solution; and measuring the current flowing between the coated electrode material and the second electrode.

In another aspect of the present invention, and in accordance with its objects and purposes, the method for quantitatively determining the presence of pinholes and other defects in a coating on the surface of a conductive electrode material, hereof includes: submersing the coated electrode material in a solution comprising a probe species dissolved in a solvent, wherein the oxidation potential of the electrode material falls outside of the electrochemical window of the solvent, while the reduction potential thereof falls within the window, and wherein the probe species has an electrochemical oxidation potential more negative than the electrochemical oxidation potential of the solvent and an electrochemical reduction potential more positive than the electrochemical reduction potential of the electrode; applying a potential to the coated electrode material relative to a second electrode submersed in the solution; and measuring the current flowing between the coated electrode material and the second electrode.

Benefits and advantages of the present invention include, but are not limited to, an in-situ, nondestructive method for quantifying the presence, or absence, of defects or pinholes in electrode surface coatings which could result in the unregulated transport of reactive and or charged species through the coating, thereby resulting in unsatisfactory device performance, without physically removing the coating from the electrode surface for subsequent testing, which would result in irreparable damage to both the coating and the energy storage device, and without otherwise inducing damage to the coating or the underlying electrode.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE INVENTION

Figure 1:
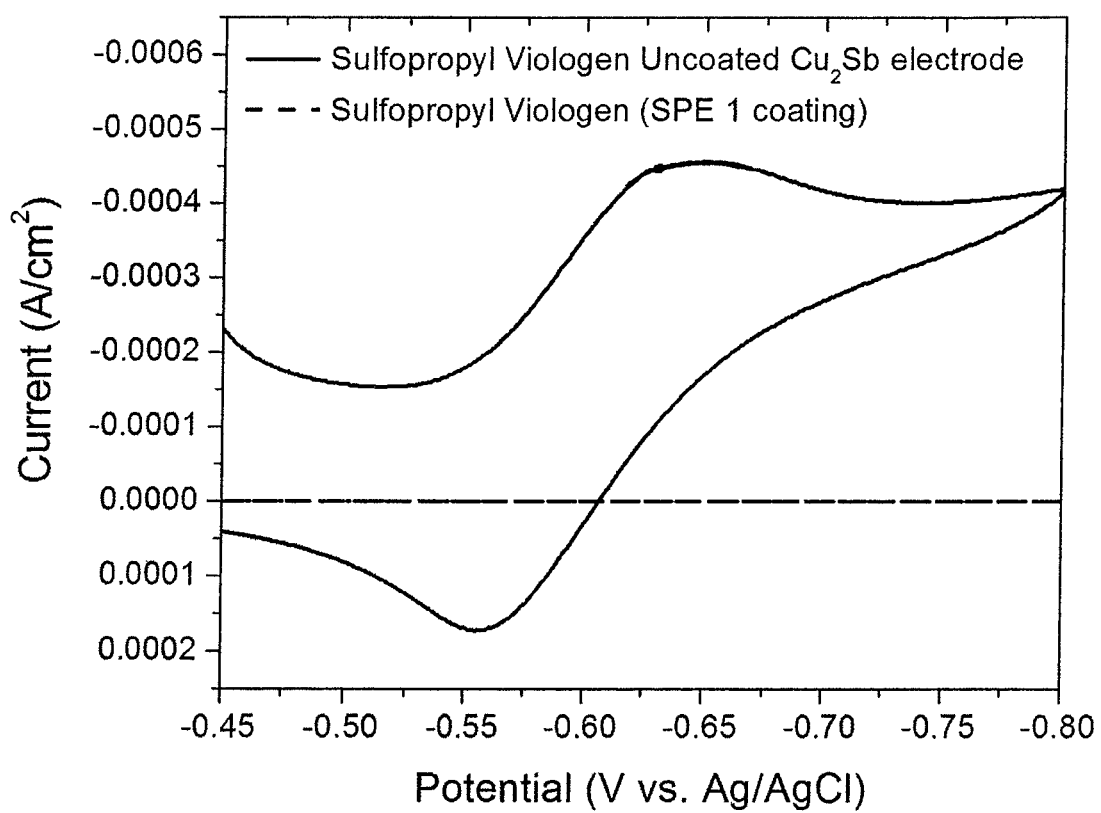
FIG. 1 is a graph of the measured current as a function of the applied potential (cyclic voltammogram) for a bare (uncoated) $Cu_2Sb$ electrode (solid curve), and for a $Cu_2Sb$ electrode coated with a solid polymer electrolyte (dashed curve) as working electrodes, immersed in a solution containing approximately 5 mM of sulfopropyl viologen (probe species) and 0.1 M $LiClO_4$ (supporting electrolyte).

Embodiments of the present invention include the use of in-line electrochemical techniques to probe coatings on the surface of three-dimensional electrodes to quantitatively determine the conformity, uniformity, and the presence of pinholes, and/or other defects in coatings, without requiring the detachment of the coating from the electrode or otherwise inducing damage to the coating. Typical solid polymer electrolyte coatings useful for lithium-ion batteries can be submicron or nanoscale in thickness and bonded to the surface of the three-dimensional electrode; therefore, removing the solid polymer electrolyte in order to prepare a free standing film for testing without inducing damage thereto, may not be possible. The present method will be demonstrated for electrode surface coatings appropriate for solid-state lithium-ion batteries, which control the transport of species that are active in the electrochemical reactions that store and/or release energy within the device, and will be referred to as solid polymer electrolytes. However, the method finds applicability for coatings having varying composition and nature, both organic and inorganic, for subsequent incorporation into electrochemical energy storage devices, such as fuel cells, batteries, and capacitors.

In accordance with the teachings of embodiments of the present invention, the determination of whether a solid polymer electrolyte that is coated onto the surface of an electrode is conformal and uniform as well as pinhole and defect free may be achieved by a solution-phase redox shutoff test. Working electrodes, as exemplified herein, and illustrated in the EXAMPLES hereinbelow, are electrically conducting, active electrode materials for lithium-ion batteries, coated with a solid polymer electrolyte, and submersed in an electrolyte solution containing a redox-active probe species. Several criteria determine the suitability of redox-active probes to be utilized without inducing electrochemical damage to either the working electrode or the solid polymer electrolyte surface coating. First, for electrodes comprising active material effective for use as the negative electrode of a lithium-ion battery, reversible oxidation and reduction of the redox probe species occurs in a potential window that is more positive than the electrochemical reduction potential of the solvent, and more negative than the oxidation potential of the working electrode. Similarly, for electrodes comprising active material effective for use as the cathode, and thus incorporated into the positive electrode of a lithium-ion battery, the reversible oxidation and reduction of the redox probe species occurs in a potential window that is more negative that the electrochemical oxidation potential of the solvent and more positive than the electrochemical reduction potential of the active material.

As an example, the electrochemical reduction potential of water on the surface of a $Cu_2Sb$ working electrode is pH dependent and, to avoid solvent reduction, the potential window for the reduction of the redox probe species would be more positive than −1 V vs. Ag/AgCl, while to ensure the $Cu_2Sb$ working electrode is not oxidized, the potential at which the species is oxidized would be more negative than −0.3 V vs. Ag/AgCl. Additionally, the species should be soluble in the solvent chosen for the redox shutoff test, which chosen solvent should not induce damage to the solid polymer electrolyte. Examples of redox probe species that meet these criteria for a $Cu_2Sb$ working electrode having solid polymer electrolytes electrodeposited onto the surface are molecules including a redox active viologen group, such as methyl viologen dichloride, which is soluble in water, a solvent demonstrated not to induce damage in the solid polymer electrolyte surface coatings described in the EXAMPLES hereinbelow, while meeting all the criteria.

The working electrode of interest is submersed in an electrolytic solution including a suitable redox probe species and solvent. A supporting electrolyte salt which is not reactive within the desired potential window may be added to facilitate charge transport within the solvent. A potential is applied to the working electrode and the corresponding current is measured. The current as a function of the applied potential for an uncoated working electrode is used as a baseline for testing solid polymer surface coatings on working electrodes. The difference in the observed current between the electrodes for a given potential is a quantitative indicator of the ability of the probe species to access the surface of the working electrode through the solid polymer electrolyte coating. Electrochemical tests may include cyclic voltammetry as well as stepped potential experiments to evaluate the diffusion coefficient of the probe species through the electrolyte. The simplest version of this test can demonstrate passivation of the working electrode by the solid polymer electrolyte coating but may not distinguish between measured current associated with the permeation of the solvated probe species through the solid polymer electrolyte surface coating from current associated with pinholes or other such defects.

Permeation of probe molecules, and thus the current response associated therewith, can vary depending on experimental conditions such as the swelling of the solid polymer electrolyte in the redox shutoff test solution, the presence of covalently bound ionic species in the polymer network, and the characteristics of the probe species. This complicates pinhole defect identification, since it may be difficult to identify the source of the resulting current. By varying the structure of the probe species, the source of the residual probe current from working electrodes with solid polymer coatings may be clarified; that is, separating current associated with pinholes from that resulting from permeation.

For solid polymer coatings, ionic redox probe species having small effective molecular diameters when compared to the diameters of pinhole defects, generate significant measured current due to permeation. One example of such a species is methyl viologen dichloride. However, current associated with permeation may be decreased by increasing the effective molecular diameter of the probe species. This may be accomplished by tethering, defined herein as attachment either through a chemical bond or through other electrostatic attractive forces such as Van der Waals bonding, redox probe species to bulky species, such as metal complexes, adamantanes, fullerenes, or nanoparticles, or by in-situ complexing a probe with a larger species (for instance viologen intercalated into a cyclodextrin pore). The result is a decrease in the probe species permeation rate through the solid polymer coating without a decrease in the current due to pinholes in the coating, as will be demonstrated in the EXAMPLES using methyl viologen dichloride, and a viologen group tethered to the surface of titanium dioxide nanoparticles.

When ionomers (which have a covalently bound ionic group in the polymeric network) are incorporated into the solid polymer electrolyte surface coating, zwitterionic probe species may be used to limit the current due to permeation. Zwitterionic probe species are species that are overall charge neutral, such as viologen disulfonate, and are effective since ionomers incorporated into the solid polymer electrolyte surface coating can efficiently shuttle oppositely charged probe molecules, such as methyl viologen, through the film resulting in a significant observed current even if the coating is conformal and uniform as well as devoid of pinholes or other such defects. Charge neutral probes are not efficiently transported through the solid polymer coating and generate much lower currents due to permeation, but do not affect the magnitude of the current associated with pinholes or similar defects, as will be demonstrated in the EXAMPLES.

Having generally described the invention, the following EXAMPLES provide greater detail.

Example 1

Effect of Size on Permeation of Probe Species:

Nondestructive, electrochemical evaluation of polyacrylonitrile-polymethyl acrylate copolymer film using the current response to an active reduction-oxidation (RedOx) probe is described. While data associated with the coating process demonstrates that a submicron-thick, solid polymer electrolyte (SPE) film comprising acrylonitrile and methyl acrylate has been deposited onto the $Cu_2Sb$ surface, it does not illustrate whether the solid polymer coating is free of pinholes, which would result in an internal short when a positive electrode is applied to complete a battery structure. The present nondestructive electrochemical RedOx evaluation utilizes water soluble sulfopropyl viologen and methyl viologen dichloride, both of which can reversibly accept and donate electrons at a potential more positive than the reduction of water and more negative than the oxidation potential of $Cu_2Sb$. Sulfopropyl viologen is a neutral species that is slightly larger than the charged methyl viologen dichloride. As discussed hereinabove, the charge and size of probe species are important properties since they affect the observed RedOx currents as a result of solvent permeation.

Electrodes having 3-D structure suitable for Li-ion batteries, as an example, have an open pore structure, or internal void space, that will allow the solution containing the Redox probe to penetrate the interior of the electrode. For example, in a nanowire array, the solution would penetrate the space between the nanowires. For a foam based 3-D structure, the solution penetrates the void space within the foam. A similar situation occurs for the $Cu_2Sb$ deposition solution, the SPE electropolymerization solution, and the positive electrode slurry. The solution containing the probe species can therefore approach the SPE in a 3-D structure, since the slurry containing the constituents of the positive electrode for fabricating the 3-D solid state lithium-ion cell can do so.

Reference will now be made in detail to the present embodiments of the invention, examples of which are illustrated in the accompanying drawings. It will be understood that the Figures are presented for the purpose of describing particular embodiments of the invention and are not intended to limit the invention thereto. A first electrode having a Cu current collector and an electrodeposited layer of $Cu_2Sb$ deposited thereon, and a second electrode having a Cu current collector and an electrodeposited layer of $Cu_2Sb$ onto which an acrylonitrile- and methyl acrylate-based solid polymer electrolyte is electropolymerized are placed into an aqueous solution containing the RedOx probe species and supporting electrolyte (0.1 M $LiClO_4$). The potential is scanned from approximately −0.45 V to about −0.80 V vs. Ag/AgCl and the current recorded. If there are pinhole defects in the solid polymer electrolyte, the RedOx probe will contact the conducting $Cu_2Sb$ surface and, depending on the polarity of the sweep, either accept or donate an electron.

Turning now to FIG. 1, a graph of the measured current in $A/cm^2$, as a function of applied potential for the first (uncoated) $Cu_2Sb$ electrode is illustrated. The reversible RedOx chemistry of the probe species on the first electrode is clearly demonstrated by the current profile (solid curve).

However, for the second electrode where the Cu$_2$Sb surface is coated with the solid polymer electrolyte, the current is reduced by almost five orders of magnitude when compared to the peak current for the uncoated first electrode (dashed curve).

Figure 2:
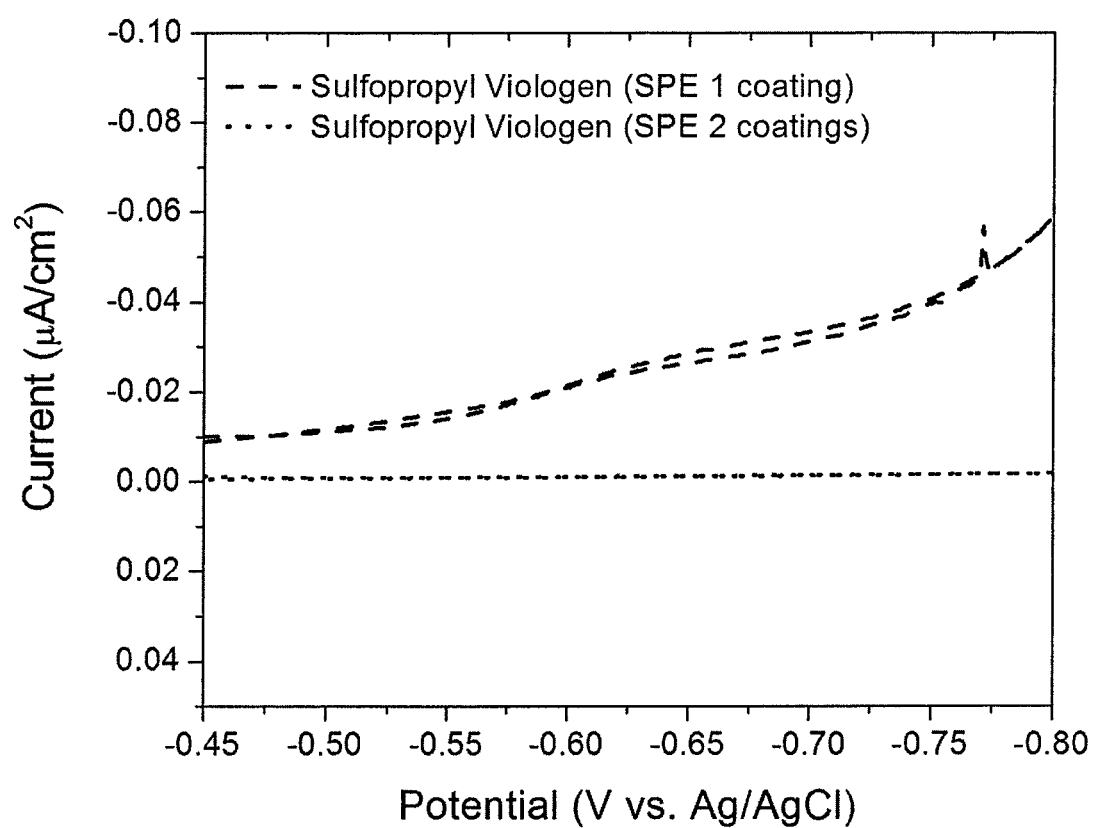
FIG. 2 is a graph including the same cyclic voltammogram data plotted in FIG. 1, hereof, where the ordinate units have been expanded from $mA/cm^2$ to $\mu A/cm^2$, and again plotted as a function of the applied potential, for illustrating the difference in current between a $Cu_2Sb$ working electrode that has been twice coated with a solid polymer electrolyte surface coating (dashed curve) when compared with a once coated identical electrode (dotted curve).

FIG. 2 is a graph including the same cyclic voltammogram data plotted in FIG. 1, hereof, where the ordinate units have been expanded from mA/cm$^2$ to μA/cm$^2$, and again plotted as a function of the applied potential, for illustrating the difference in current between a Cu$_2$Sb working electrode that has been twice coated with a solid polymer electrolyte surface coating (dashed curve) when compared with a once coated identical electrode (dotted curve). The additional decrease in current to below measurable values indicates that the acrylonitrile-methyl acrylate copolymer twice coated on the Cu$_2$Sb surface is indeed conformal and uniform as well as free of pinholes and similar defects.

Figure 3:
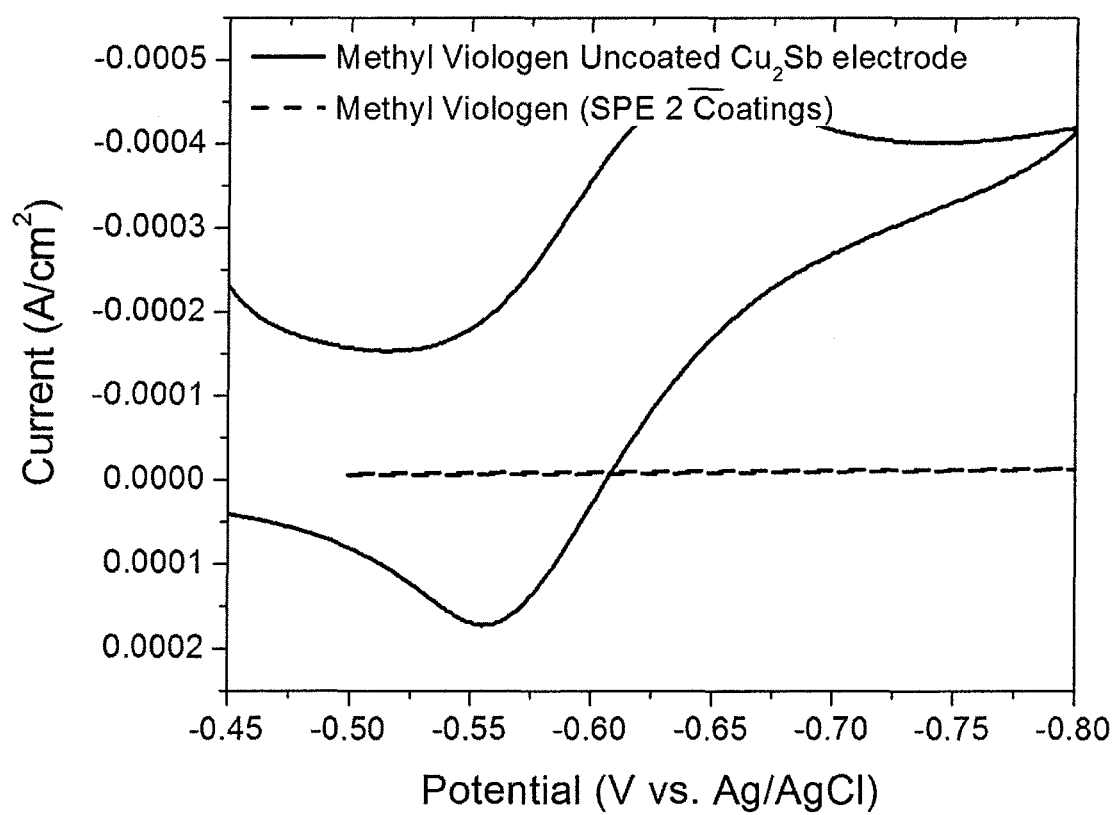
FIG. 3 illustrates cyclic voltammograms collected from a solution containing approximately 5 mM methyl viologen dichloride (probe species) and 0.1 M $LiClO_4$ (supporting electrolyte) for both bare (uncoated) $Cu_2Sb$ (solid curve) and $Cu_2Sb$ coated with a solid polymer electrolyte surface coating (dashed curve), as working electrodes.
Figure 4:
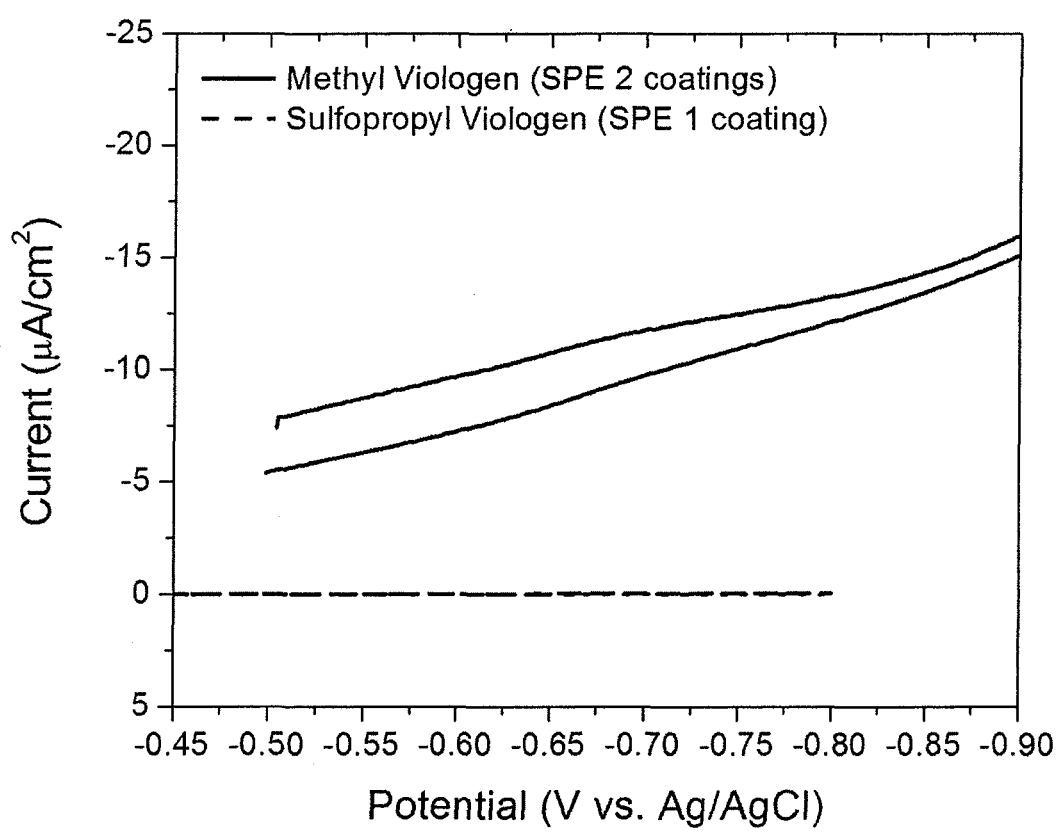
FIG. 4 illustrates cyclic voltammogram data from FIGS. 2 and 3, hereof, where the ordinate units have been expanded from $mA/cm^2$ to $\mu A/cm^2$ to illustrate the difference in current between the methyl viologen dichloride probe species (solid curve) and the sulfopropyl viologen probe species (dashed curve).

FIG. 3 illustrates voltammograms were taken in a similar manner to those for FIGS. 1 and 2 hereof, except that the probe species was methyl viologen dichloride. As may be observed in FIG. 3, a large decrease in current occurs when a Cu$_2$Sb working electrode is coated with the electropolymerized acrylonitrile- and methyl acrylate-based solid polymer electrolyte (dashed curve) over that for a bare (uncoated) Cu$_2$Sb electrode (solid curve). FIG. 4 demonstrates the increased permeation into the SPE for smaller, charged solvated probe species when comparing the observed current from the methyl viologen dichloride species to that observed from the sulfopropyl viologen probe species; that is, a larger degree of permeation into the film is observed with methyl viologen when compared to sulfopropyl viologen. Probe permeation is an undesirable result as chemically active species in the form of the probe species could remain trapped in the solid polymer electrolyte coating and thus subsequently incorporated into the final device, which might negatively impact device performance. The following examples are therefore focused synthesizing a heterostructure that contains the active probe species tethered, or otherwise attached, to a structure that totally prevents permeation, such as a metal oxide nanoparticle, while remaining effective as a probe for conformity, uniformity, pinholes and defects.

Example 2

Figure 5:
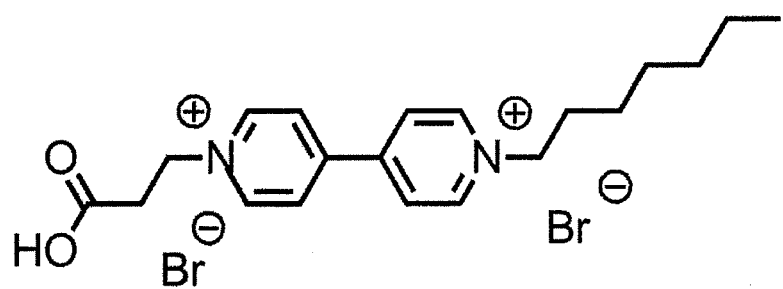
FIG. 5 illustrates the chemical structure of N-(1-heptyl, N'-(3-carboxypropyl)-4,4'-bipyridinium bromide ($HVP^{2+}$).
Figure 6:
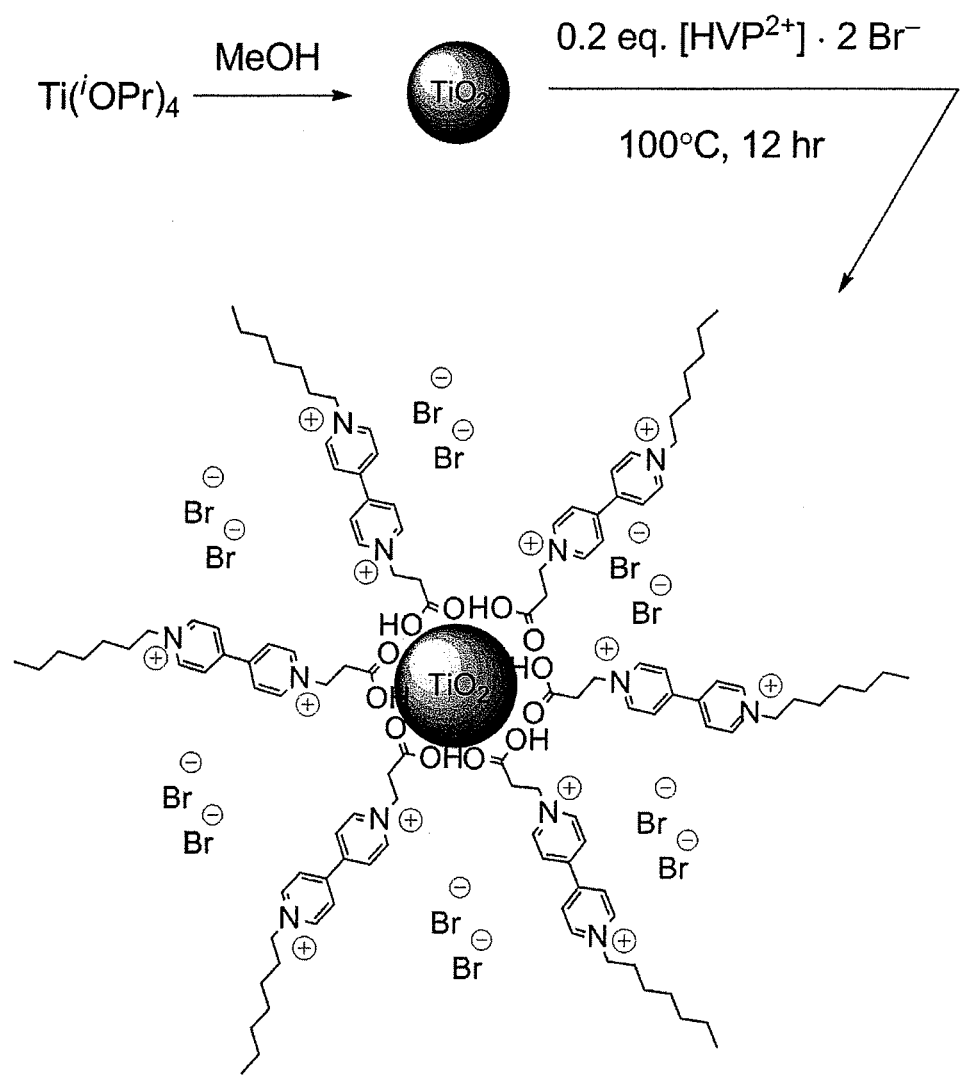
FIG. 6 illustrates an embodiment of the synthesis of the $HVP^{2+}/TiO_2$ heterostructure.

Attachment of an Effective Probe to a Nanoparticle:

The redox active species, N-(1-heptyl, N'-(3-carboxypropyl)-4,4'-bipyridinium) bromide, HVP$^{2+}$, was attached to the surface of titanium dioxide (TiO$_2$) nanoparticles, as will be described hereinbelow. HVP$^{2+}$ is a long-chain, redox-active organic molecule containing a carboxylic acid group at one end that can bind to metal oxide surfaces through Van der Waals type bonding, as illustrated in FIG. 5, hereof. The redox activity of HVP$^{2+}$ is imparted by the incorporation of a dicationic 4,4'-bipyridinium moiety in the interior of the molecule that exhibits two one-electron redox couples at approximately −700 mV and −850 mV vs. Ag/AgCl. As shown in FIG. 6, hereof, attachment of HVP$^{2+}$ to the surface of titania nanoparticles was accomplished by solvothermal decomposition of titanium isopropoxide, Ti($^i$PrO)$_4$, in a solution of methanolic HVP$^{2+}$ at 100° C. Following the removal of excess HVP$^{2+}$ by precipitation with diethyl ether, the colloidal suspension of HVP$^{2+}$-TiO$_2$ nanoparticles was analyzed by X-ray diffraction (XRD), FT-IR, and $^1$H NMR.

The XRD pattern for an evaporated film of HVP$^{2+}$-TiO$_2$ nanoparticles contains no significant peaks, indicating that the particles are non-crystalline. For comparison, a separate sample of TiO$_2$ prepared by solvothermal decomposition of Ti($^i$PrO)$_4$ in the absence of HVP$^{2+}$ displayed a similar XRD pattern.

Figure 7:
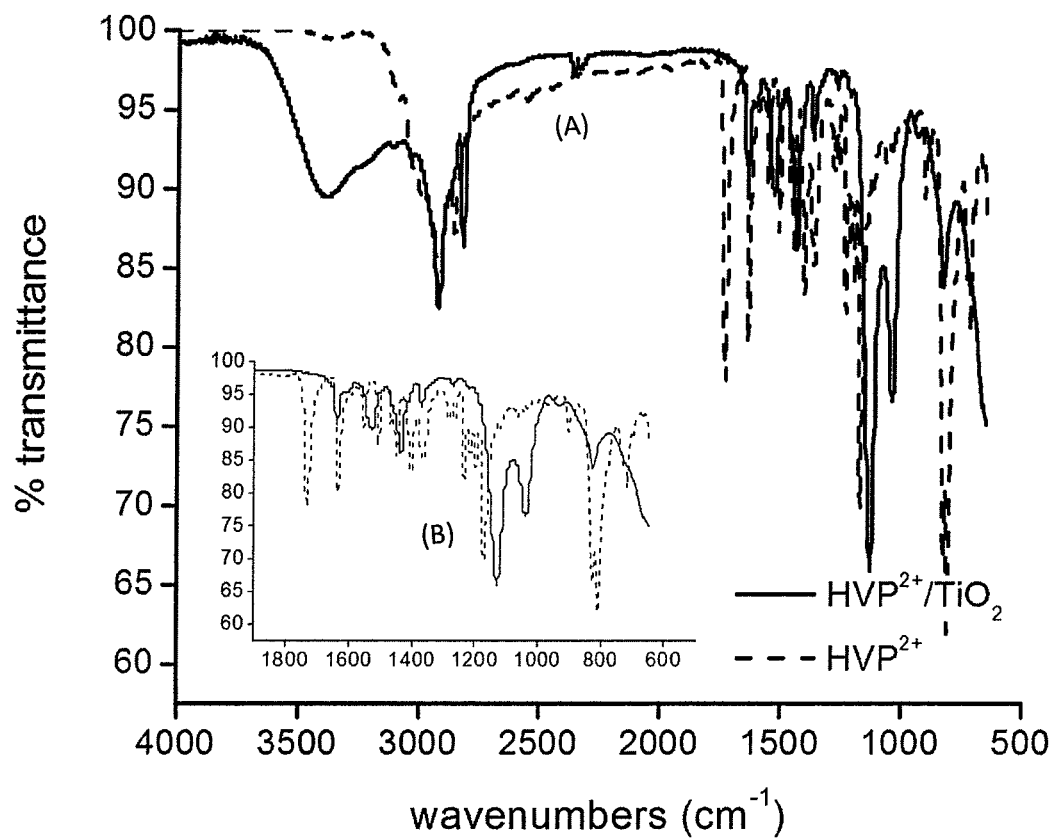
FIG. 7 shows Infrared (IR) spectra of $HVP^{2+}$ (dash trace) and the $HVP^{2+}/TiO_2$ heterostructure (solid trace).
Figure 8:
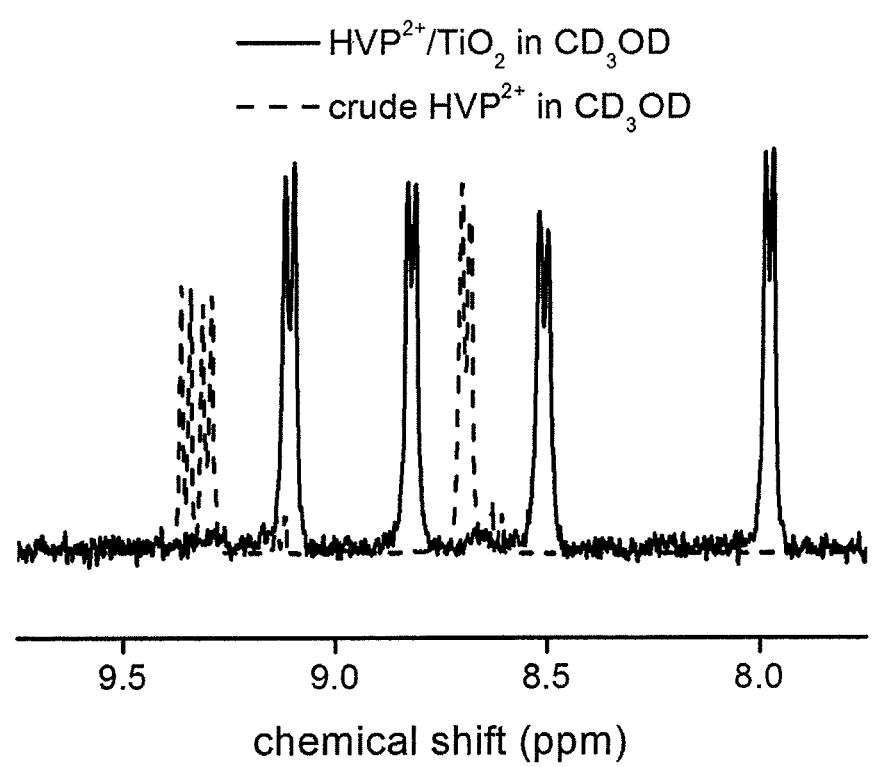
FIG. 8 shows the aromatic region of the $^1H$ NMR for $HVP^{2+}$ (dash trace) and the $HVP^{2+}/TiO_2$ heterostructure (solid trace) in $d_4$-methanol, the resonances at about 9.1 and 8.6 ppm in the $HVP^{2+}$ spectrum correspond to a 5 mol % impurity identified as N,N'-di(heptyl)-4,4'-bipyridinium bromide.

The IR spectra of free HVP$^{2+}$ and an evaporated film of HVP$^{2+}$-TiO$_2$ are shown in FIG. 7 (Curve (A)), hereof. The spectrum of unbound HVP$^{2+}$ contains resonances at 3100-2855 cm$^{-1}$ that correspond to O—H and aliphatic C—H stretching vibrations, as well as a sharp resonance at 1732 cm$^{-1}$ that can be assigned to the $v_{C=O}$ stretch. However, the peak at 1732 cm$^{-1}$ is notably absent in the IR spectrum of an evaporated film of HVP$^{2+}$-TiO$_2$, while the aliphatic peaks are retained which is consistent with the presence of surface-bound HVP$^{2+}$. The spectrum for HVP$^{2+}$-TiO$_2$ also contains asymmetric ($v_a$) and symmetric ($v_s$) stretching modes for the bound carboxylate anion at 1527 cm$^{-1}$ and 1437 cm$^{-1}$, respectively. The change in the asymmetric and symmetric stretching modes ($\Delta v_{a-s}$) metric has been used to identify the carboxylate binding mode; for the HVP$^{2+}$-TiO$_2$ heterostructure, the $\Delta v_{a-s}$=91 which suggests a bidentate chelating mode of HVP$^{2+}$ bonding to the TiO$_2$ surface. The inset (Curve (B)) shows detail of the fingerprint region showing the lack of free HVP$^{2+}$ in the heterostructure. For example, the absence of a free C=O stretch 1732 cm$^{-1}$ in the solid trace may be observed.

Evaporation of a colloidal suspension of HVP$^{2+}$-TiO$_2$ affords a light-yellow solid than can be taken up in polar solvents such as acetonitrile, methanol, and acidic water. A suspension of HVP$^{2+}$-TiO$_2$ in deuterated methanol, CD$_3$OD, was analyzed by $^1$NMR, and the spectrum contains resonances from surface-bound HVP$^{2+}$ that are shifted relative to the free ligand as shown in FIG. 7. Most notable are the resonances for the 4 chemically unique protons on the bipyridinium rings. In the free ligand, the peaks are observed as two sets of overlapping doublets while in the heterostructure they become four well-separated doublets over a broader range of chemical shifts.

N-(1-heptyl, N'-(3-carboxypropyl)-4,4'-bipyridinium) bromide (HVP$^{2+}$) was synthesized as previously described. As received batches of HVP$^{2+}$ contained a small amount (5 mol %) of an impurity identified as N,N'-di(heptyl)-4,4'-bipyridinium bromide as indicated by $^1$H NMR analysis. The impurity was present in the commercially obtained starting material (1-heptyl-4-(4'-pyridyl)pyridinium bromide). All other chemicals were purchased commercially and used as received.

Titanium (IV) isopropoxide (473.4 mg, 1.666 mmol) was added to a yellow solution of HVP$^{2+}$ (195.2 mg, 0.400 mmol) in methanol (10 mL) in a 50 mL glass beaker, with stirring, thereby causing TiO$_2$ to precipitate from solution. The reaction mixture was transferred to a 23 mL Teflon PARR liner which was then sealed tightly in a PARR bomb. The bomb was heated to 100° C. at 4° C./min and held at 100° C. for 12 hours before the oven was shut off. After cooling to room temperature, diethyl ether (40 mL) was added to the clear yellow solution, causing a pale yellow solid (HVP$^{2+}$) to precipitate. The mixture was separated by centrifugation (3500 rpm, 10 min.) and the volume of the supernatant was reduced to about 10 mL by evaporation to afford a clear, nearly colorless dispersion of the HVP$^{2+}$/TiO$_2$ heterostructure. An aliquot of the HVP$^{2+}$-TiO$_2$ dispersion was evaporated to dryness, then dissolved in d$_4$-methanol for NMR analysis. IR (ATR): 3379 (m), $v_{C—H}$ 2922 (m), 2821 (m), $v_{C=O}$ 1639 (m), 1613 (w), $v_a$ 1528 (m), $v_s$ 1437 (m), 1370 (w), 1272 (w), 1221 (w), 1130 (s), 1040 (s), 935 (w), 827 (m) cm$^{-1}$. $^1$H NMR (CD$_3$OD): δ 9.13 (d, 2H, py-H), 8.84 (d, 2H, py-H), 8.53 (d, 2H, py-H), 8.00 (d, 2H, py-H), 4.50 (t, 2H, —CH$_2$), 2.06 (br s, 2H, —CH$_2$), 1.43 (br s, 4H, —CH$_2$), 1.34 (br s, 4H, —CH$_2$), 1.16 (m, 4H, —CH$_2$), 0.91 (t, 3H, —CH$_3$).

$^1$H NMR spectra were recorded on Varian spectrometers (300 MHz or 400 MHz) at 23° C. All $^1$H chemical shifts were calibrated internally to the CHCl$_3$ impurity in d-chloroform. Infrared spectra were recorded using a Nicolet 380 FT-IR equipped with a Smart Performer ZnSe attenuated total reflectance accessory. XRD spectra were measured with a Scintag X-2 diffractometer using Cu Kα radiation. Electrochemical data were recorded using a Gamry Instruments Reference 3000 potentiostat/galvanostat.

All electrochemical experiments were carried out under a blanket of N$_2$ in 0.1 M HCl electrolyte using a frit-separated H-cell. One cell compartment contained the working and Ag/AgCl (saturated KCl) reference electrodes and a second compartment contained the counter electrode (Pt mesh). Prior to each measurement, the solution was thoroughly mixed and degassed by sparging with dinitrogen.

Example 3

Figure 9:
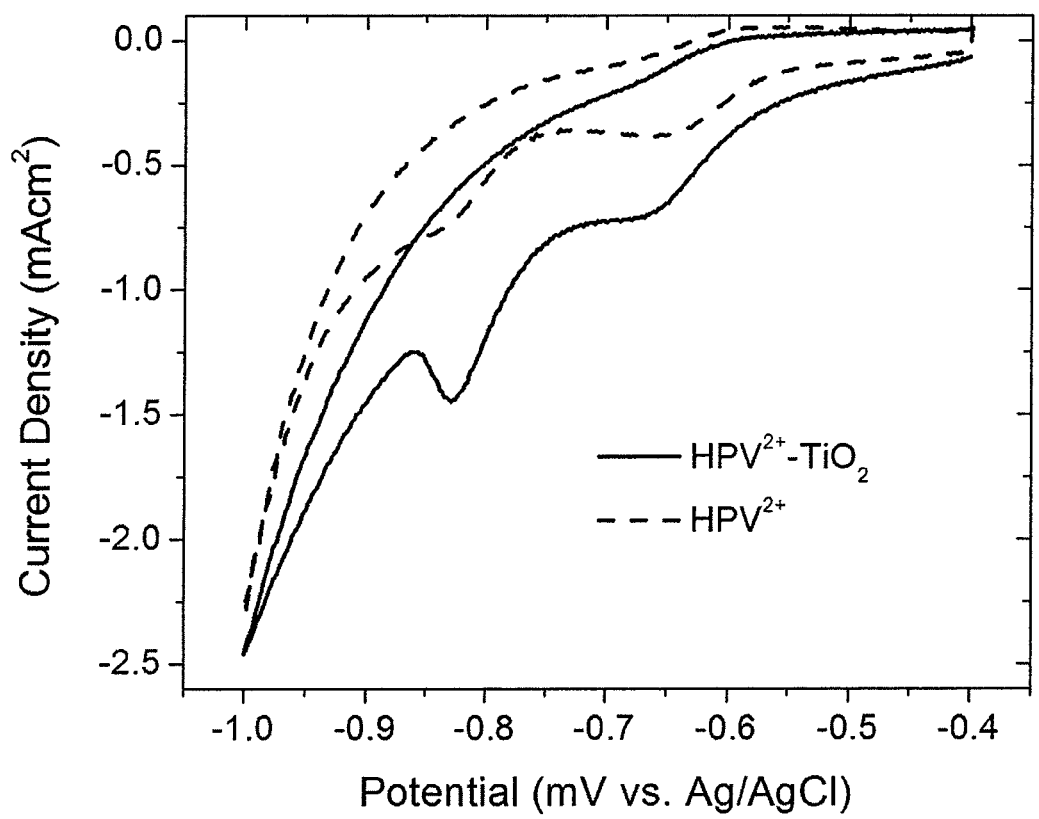
FIG. 9 are cyclic voltammograms of a 9% (v/v) dispersion of $HVP^{2+}$-$TiO_2$ (solid curve) and $HVP^{2+}$ (dashed curve) in 0.1 M HCl using a 1.8 $cm^2$ $Cu_2Sb$ working electrode, at a scan rate of 50 mV/s.

Demonstration of Electrochemical Activity of Heterostructure:

To demonstrate that the above described heterostructure is electrochemically active in the desired potential window, the electrochemical behavior of a 2 mM solution of free HVP$^{2+}$ in 0.1 M HCl was analyzed using both a glassy carbon disk and Cu$_2$Sb electrodeposited onto Cu foil as working electrodes. For each electrode, two redox couples were observed; a quasi-reversible event at $E_{1/2}$=−0.63 V vs. Ag/AgCl and an irreversible reduction at $E_p$=−0.85 V vs. Ag/AgCl=50 mV/s). The potentials for the redox couples shift slightly upon attachment to a TiO$_2$ nanoparticle. For a 9% (v/v) solution of HVP$^{2+}$-TiO$_2$ dispersion in 0.1 M HCl, the redox couples are observed at $E_{1/2}$=−0.68 V and $E_p$=−0.85 V vs. Ag/AgCl=50 mV/s). When Cu$_2$Sb is the working electrode, the potentials are $E_{1/2}$=−0.64 V and $E_p$=−0.83 V vs. Ag/AgCl. As shown in FIG. 9, while attaching the HVP$^{2+}$ species to the titanium dioxide nanoparticles results in a slight shift in the reduction and oxidation potentials (solid curve) over that for the unattached HVP$^{2+}$ species (dashed curve), the activity of the heterostructure remains within the desired potential window and is soluble in a solvent that does not induce damage to the acrylonitrile- and methyl-acrylate-based solid polymer electrolyte coating, thereby meeting all of the required criteria for a functional probe species.

Example 4

Figure 10:
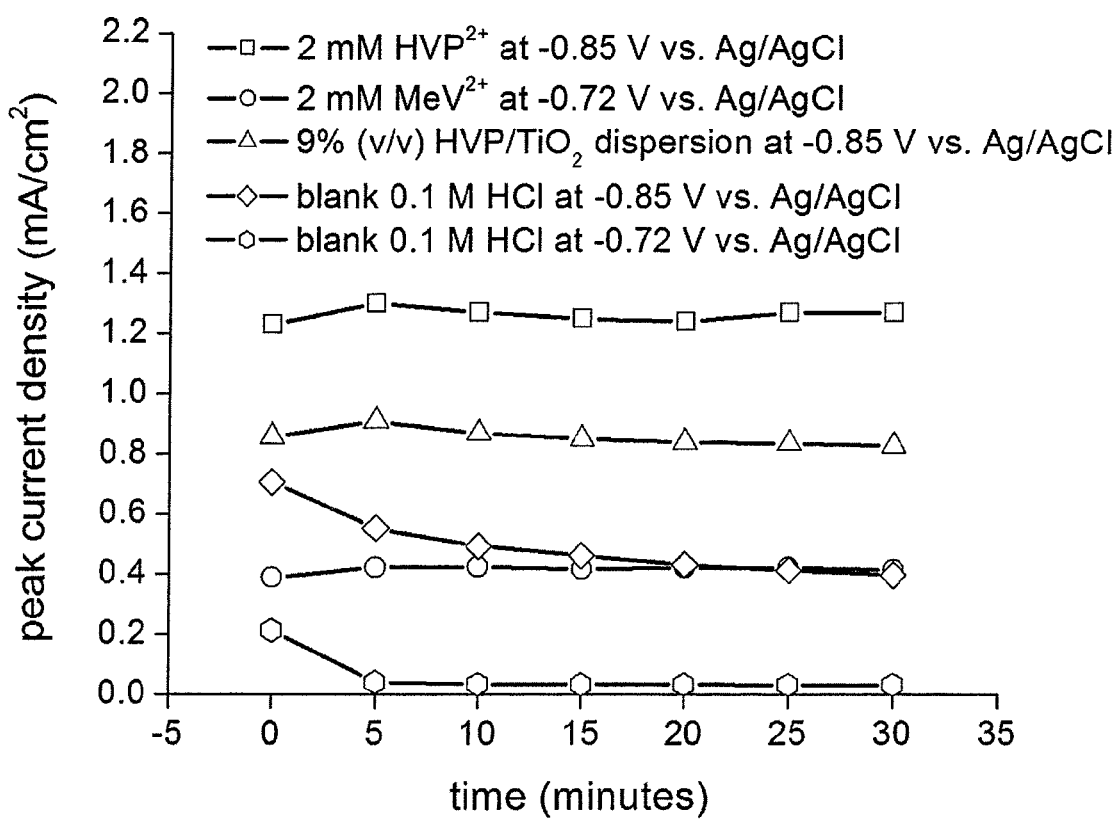
FIG. 10 is a graph of peak anodic current densities as a function of time for $HVP^{2+}$, $MeV^{2+}$, and $HVP^{2+}$ on bare $Cu_2Sb$ foil electrodes.

Prevention of Permeation by Heterostructure:

Cyclic voltammograms were recorded as a function of time using Cu$_2$Sb electrodes coated with an acrylonitrile- and methyl acrylate-based solid polymer electrolyte coating submersed in the electrolytic solution. Additionally, voltammograms were recorded in 2 mM solutions of free HVP$^{2+}$ and the relatively smaller charged methyl viologen dichloride (MeV$^{2+}$) species which exhibits a reversible redox couple at $E_{1/2}$=−0.66 V with the peak current density occurring at −0.72 V vs. Ag/AgCl. As shown in FIG. 10, hereof, the observed peak current density for each redox-active species remains approximately constant during a 30 min. measurement. Additionally, the peak currents recorded for the active probe species are higher than the current recorded for the blank at the corresponding peak current potential; that is −0.85 V vs. Ag/AgCl for the HVP$^{2+}$ species and −0.72 V vs. Ag/AgCl for methyl viologen dichloride.

Figure 11:
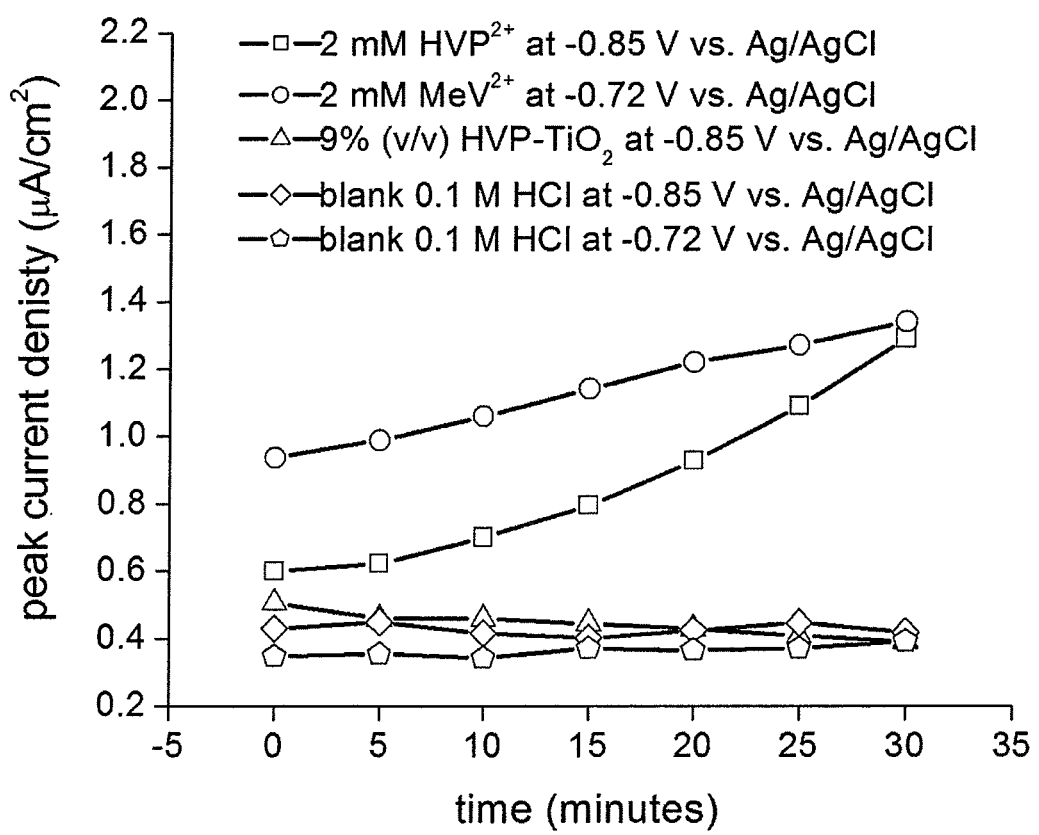
FIG. 11 is a graph of peak anodic current densities as a function of time for $HVP^{2+}$, $MeV^{2+}$, and $HVP^{2+}$ on $Cu_2Sb$ foil electrodes coated with a polyacrylonitrile-polymethyl acrylate co-polymer.

For the above described acrylonitrile and methyl acrylate based solid polymer electrolyte coated Cu$_2$Sb electrodes, the initial current densities are significantly reduced relative to those for the bare Cu$_2$Sb electrode in accordance with the insulating properties of the solid polymer surface coating. However, there is an increase over time in the peak current densities for HVP$^{2+}$ and MeV$^{2+}$ as the molecules permeate the polymer coating and diffuse to the surface of the Cu$_2$Sb electrode, thereby resulting in an electrochemical reduction reaction. This may be observed from the data displayed in FIG. 11, hereof. By contrast, there is little current observed relative to the background over time for the heterostructure, thereby demonstrating that the HVP$^{2+}$-TiO$_2$ heterostructure does not permeate the solid polymer electrolyte. The utilization of a heterostructure therefore prevents the chemically active probe species from becoming entrained and therefore trapped in the solid polymer electrolyte coating. That the probe species does not permeate into the solid polymer coating ensures that a chemically active species that might be detrimental to device performance is not inadvertently incorporated into the final electrochemical energy storage device.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for quantitatively determining the presence of pinholes in an electrically insulating coating that has been electrochemically deposited on the surface of a conductive electrode material, comprising:
    submersing the coated electrode material in a solution comprising a probe species dissolved in a solvent chosen such that said conductive electrode material has a reduction potential outside the electrochemical window of the solvent, wherein the probe species has a reversible electrochemical reduction potential more positive than the electrochemical reduction potential of the solvent and a reversible electrochemical oxidation potential more negative than the electrochemical oxidation potential of the electrode material;
    applying a potential to the coated electrode material relative to a second electrode submersed in the solution; and
    measuring the current flowing between the coated electrode material and the second electrode.

2. The method of claim 1, wherein the applied potential is more positive than the electrochemical reduction potential of the solvent and more negative than the electrochemical oxidation potential of the conductive electrode.

3. The method of claim 1, wherein the applied potential is scanned from a potential more negative than the electrochemical oxidation potential of the conductive electrode and more positive than the electrochemical oxidation potential of the probe species, to a potential more positive than the electrochemical reduction potential of the solvent and more negative than the electrochemical reduction potential of the probe species, and back to a potential more negative than the electrochemical oxidation potential of the conductive electrode and more positive than the electrochemical oxidation potential of the probe species.

4. The method of claim 3, wherein the scan rate is between 0.001 $Vs^{-1}$ and 1 $Vs^{-1}$.

5. The method of claim 1, further comprising the steps of:
submersing an uncoated conductive electrode material in the solution;
applying the potential to the uncoated electrode material relative to a second electrode submersed in the solution;
measuring the current flowing between the uncoated electrode material and the second electrode; and
comparing the measured current of the coated electrode material with the measured current of the uncoated electrode material at the applied potential.

6. The method of claim 1, further comprising the step of tethering the probe species to a larger species effective for reducing the permeation of the probe through the coating.

7. The method of claim 6, wherein the probe species is complexed with the larger species.

8. The method of claim 6, wherein the larger species is chosen from metal complexes, adamantanes, fullerenes, and nanoparticles.

9. The method of claim 6, wherein the probe species comprises a viologen group.

10. The method of claim 9, wherein the viologen group is tethered to the surface of titanium dioxide nanoparticles.

11. The method of claim 1, further comprising the step of adding a supporting electrolyte salt to the solution for facilitating charge transport within the solution, wherein the electrolyte salt is not reactive within the electrochemical oxidation potential and electrochemical reduction potential of the probe species.

12. The method of claim 11, wherein the electrode material comprises $Cu_2Sb$, the coating comprises a polyacrylonitrile-polymethyl acrylate copolymer film, the probe species comprises a viologen, and the electrolyte salt comprises $LiClO_4$.

13. A method for quantitatively determining the presence of pinholes in an electrically insulating coating that has been electrochemically deposited on the surface of a conductive electrode material, comprising: submersing the coated electrode material in a solution comprising a probe species dissolved in a solvent chosen such that the conductive electrode material has an oxidation potential outside the electrochemical window of the solvent, wherein the probe species has a reversible electrochemical oxidation potential more negative than the electrochemical oxidation potential of the solvent and a reversible electrochemical reduction potential more positive than the electrochemical reduction potential of said electrode material; applying a potential to the coated electrode material relative to a second electrode submersed in the solution; and measuring the current flowing between the coated electrode material and the second electrode.

14. The method of claim 13, wherein the applied potential is more negative than the electrochemical oxidation potential of the solvent and more positive than the electrochemical reduction potential of the conductive electrode.

15. The method of claim 13, wherein the applied potential is scanned from a potential more positive than the electrochemical reduction potential of the conductive electrode but more negative than the electrochemical reduction potential of the probe species to a potential more negative than the electrochemical oxidation potential of the solvent and more positive than the electrochemical oxidation potential of the probe species, and back to a potential more positive than the electrochemical reduction potential of the conductive electrode and more negative than the electrochemical reduction potential of the probe species.

16. The method of claim 15, wherein the scan rate is between 0.001 $Vs^{-1}$ and 1 $Vs^{-1}$.

17. The method of claim 13, further comprising the steps of:
submersing an uncoated conductive electrode material in the solution;
applying the potential to the uncoated electrode material relative to a second electrode submersed in the solution;
measuring the current flowing between the uncoated electrode material and the second electrode; and
comparing the measured current of the coated electrode material with the measured current of the uncoated electrode material at the applied potential.

18. The method of claim 13, further comprising the step of tethering the probe species to a larger species effective for reducing the permeation of the probe through the coating.

19. The method of claim 18, wherein the probe species is complexed with the larger species.

20. The method of claim 18, wherein the larger species is chosen from metal complexes, adamantanes, fullerenes, and nanoparticles.

21. The method of claim 18, wherein the probe species comprises a viologen group.

22. The method of claim 21, wherein the viologen group is tethered to the surface of titanium dioxide nanoparticles.

23. The method of claim 13, further comprising the step of adding a supporting electrolyte salt to the solution for facilitating charge transport within the solution, wherein the electrolyte salt is not reactive within the electrochemical oxidation potential and electrochemical reduction potential of the probe species.

24. The method of claim 23, wherein the electrode material comprises $Cu_2Sb$, the coating comprises a polyacrylonitrile-polymethyl acrylate copolymer film, the probe species comprises a viologen, and the electrolyte salt comprises $LiClO_4$.

* * * * *